(12) United States Patent
Golding et al.

US006258840B1

(10) Patent No.: US 6,258,840 B1
(45) Date of Patent: Jul. 10, 2001

(54) ANALOGUES OR DERIVATIVES OF QUERCETIN (PRODRUGS)

(75) Inventors: Bernard Thomas Golding, Newcastle Upon Tyne; Roger John Griffin, Morpeth; Charmaine Paulina Quarterman, Redditch; John Alfred Slack, Solihull; Jonathan Gareth Williams, Nuneaton, all of (GB)

(73) Assignee: Cobra Therapeutics Limited (GB)

( * ) Notice: Subject to any disclaimer, the term of this patent is extended or adjusted under 35 U.S.C. 154(b) by 0 days.

(21) Appl. No.: 09/202,948

(22) PCT Filed: Jun. 27, 1997

(86) PCT No.: PCT/GB97/01727

§ 371 Date: Jul. 20, 1999

§ 102(e) Date: Jul. 20, 1999

(87) PCT Pub. No.: WO97/49693

PCT Pub. Date: Dec. 31, 1997

(30) Foreign Application Priority Data

Jun. 27, 1996 (GB) .................................................. 9613455

(51) Int. Cl.$^7$ .......................... A01N 43/32; C07D 411/76
(52) U.S. Cl. ........................................... 514/457; 549/403
(58) Field of Search .............................. 514/457; 549/403

(56) References Cited

U.S. PATENT DOCUMENTS

| 4,202,825 | 5/1980 | Tayá et al. | 260/345.2 |
|---|---|---|---|
| 4,352,792 | 10/1982 | Ishitsuka et al. | 424/180 |

FOREIGN PATENT DOCUMENTS

| 0 019 081 | 11/1980 | (EP) . |
|---|---|---|
| 0 505 937 | 9/1992 | (EP) . |

OTHER PUBLICATIONS

Conners et al. "Prodrugs in Cancer Chemotherapy", *Stem Cells*, vol. 13, (1995), pp. 501–511.

Hansen et al., "Phenyl Carbamates of Amino Acids as Prodrug forms for Protecting Phenols Against First–pass Metabolism", *Int. J. Pharm.*, vol. 81, (1992), pp. 253–261.

Ueda, et al., "Design, Synthesis and Antiinflammatory Activity of aNew Indomethacin Ester", *Chem. Pharm. Bull.*, vol. 39, No. 3, (1991), pp. 679–684.

Anderson et al., "Synthesis and Antieoplastic Activity of Biss[[[(alkylamino)carbonyl]oxy]methyl]–Substituted 3–Pyrrolines as Prodrugs of Tumor Inibitory Pyrrole Bis-(carbamates)" *J. Med. Chem.*, vol. 29, No. 11, (1986), pp. 2241–2249.

Jurd. "Plant Polyphenols. V. Selective Alkylation of the 7–Hydroxyl Group in Polyhydroxyfavones", *J. Am. Chem. Soc.*, vol. 80, (1958), pp. 5531–5536.

Connors et al., "Prodrugs in Cancer Therapy", *Stem Cells*, (1995), Sep.; 13(5), pp. 501–511.

*Primary Examiner*—Alan L. Rotman
*Assistant Examiner*—Raymond Covington
(74) *Attorney, Agent, or Firm*—Woodcock Washburn Kurtz Mackiewicz & Norris LLP

(57) ABSTRACT

Novel carbamate ester analogues or derivatives of Quercetin (prodrugs) are provided which have enhanced aqueous solubility and which are especially suitable for use as biodegradable prodrugs in pharmaceutical compositions formulated for clinical use.

22 Claims, No Drawings

US 6,258,840 B1

ANALOGUES OR DERIVATIVES OF QUERCETIN (PRODRUGS)

This application is a 371 of PCT/GB97/01727 filed Jun. 27, 1997.

FIELD OF THE INVENTION

The present invention relates to the field of biochemistry and medicine. More particularly it relates to Quercetin analogues or derivatives and preparations thereof. These compounds are potentially useful in tumour chemotherapy, treatment of inflammation and allergy.

BACKGROUND

The flavonoid Quercetin (3,3',4',5,7-pentahydroxyflavone) has been shown to inhibit the activity of a variety of enzymes including the calcium- and phospholipid dependent protein kinase (protein kinase C) in vivo and in vitro. Furthermore, it synergistically enhances the antiproliferative activity of cis-diaminedichloroplatinum II (cis-DDP) both in vitro and in vivo and therefore is of interest as a promising therapeutic agent for use in the chemotherapy of human tumours. However, Phase I clinical trials have proved problematic owing to the limited solubility of Quercetin in pharmaceutically acceptable solvents, and this characteristic has prevented its further clinical development.

SUMMARY OF THE INVENTION

The present invention has developed from efforts to produce analogues or derivatives of Quercetin having greater aqueous solubility, more suitable for use in pharmaceutical formulations and capable of acting as prodrugs which can be biologically degraded or broken down to release Quercetin within the body after being administered to a patient in need of treatment.

More specifically, from one aspect, the present invention provides compounds of the structural formula I below:

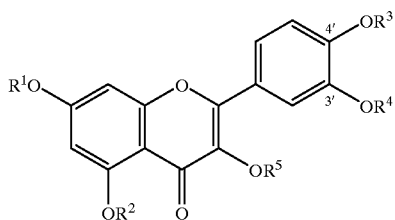

I and pharmaceutically acceptable salts thereof
wherein
one of $R^1$, $R^2$, $R^3$, $R^4$ and $R^5$ is an amino acid carbamate group $CONHCH(R^6)CO_2H$ and the remainder are each hydrogen,
and wherein
$R^6$ is hydrogen or $C_{1-4}$ lower alkyl, e.g. methyl.

Preferred compounds of this invention comprise those compounds wherein $R^1$, $R^2$, $R^3$ and $R^5$ are each hydrogen and $R^4$ is $CONHCH_2CO_2H$, and those compounds wherein $R^1$, $R^2$, $R^4$ and $R^5$ are each hydrogen and $R^3$ is $CONHCH_2CO_2H$. The invention also provides salts of these acid Quercetin analogues. Apart from alkali metal and ammonium salts, amine salts, for example amine salts formed with amino sugars, especially N-alkyl amino sugars such as N-methylglucamine, are of particular interest.

In general, the compounds of the invention as defined above are novel analogues or derivatives of Quercetin which have enhanced aqueous solubility and which are especially suitable for use as biodegradable prodrugs in pharmaceutical compositions formulated for clinical use.

Thus, the invention also includes pharmaceutical compositions comprising or containing such novel analogues or derivatives providing prodrugs made up or formulated for administration in any suitable manner in the course of medical or veterinary treatment, for example parentally (including intravenously, intramuscularly and subcutaneously) or orally. Such compositions containing or incorporating, conveniently in unit dosage form, therapeutically effective non-toxic amounts of the prodrug compound, or the equivalent of therapeutically effective non-toxic amounts of the active drug compound, together possibly with at least one other ingredient providing a compatible pharmaceutically acceptable additive, carrier, diluent or excipient, may be prepared by any of the methods well known in the art of pharmacy.

The invention also provides new processes for preparing at least some of the compounds referred to above involving in some cases certain novel intermediate compounds.

MORE DETAILED DESCRIPTION

The invention will be further described and exemplified with specific reference to the preparation and properties of Quercetin carbamate ester derivatives or analogues, particularly N-methylglucamine salts, referred to as meglumine salts, of 3'-[(N-carboxymethyl)carbamoyloxy]-3,4',5,7-tetrahydroxyflavone and the corresponding 4' isomer.

It has been found that these carbamate esters of Quercetin are reasonably stable in aqueous solution but they will degrade to Quercetin under physiological conditions.

First, there is presented below the analytical conditions that were used to demonstrate that the meglumine salts of 3' and 4'-[(N-carboxymethyl) carbamoyloxy]-3,4'(3'),5,7-tetrahydroxyflavone have the desired properties for formulation for clinical trial. Then, there are presented details of a process for synthesising these analogues or derivatives of Quercetin.

Analytical Methodology-Non Biological samples

The following conditions were used to analyse the meglumine salts of 3' and 4'-((N-carboxymethyl)carbamoyloxy)-3,4'(3'),5,7-tetrahydroxyflavone.

| HPLC | |
|---|---|
| Column: | Primesphere HC C-18, 5 µm, 250 × 3.2 mm. |
| Mobile phase: | 45% Methanol in 3mM ammonium acetate pH 3.4 |
| Flow rate: | 0.5 ml/min |
| Temperature: | Ambient |
| Detection: | UV at 368 nm |
| Injection volume: | 60 µl of a 100 mg/ml solution in water (6 µg of sample was injected onto the column; 6 µg was passed through the detector and using a 1:1 splitter, 3 µg was passed, in series, to the mass spectrometer. |
| Retention times: | Component 1–15.8 minutes |
| | Component 2–16.7 minutes |

Mass Spectrometry

Cone voltage: 30V

Ionisation mode: Electrospray positive

Flow rate: ≈0.25 ml/min (The flow was split 1:1)

Aqueous Solubility

The solubility of the meglumine salts of 3' and 4'-[(N-carboxymethyl)carbamoyloxy]-3,4'(3'),5,7-tetrahydroxyflavone has been determined by HPLC and shown to be in excess of 10 mg/ml.

Aqueous Stability

3'/4'-((N-Carboxymethyl)carbamoyloxy)-3,4'(3'),5,7-tetrahydroxyflavone shows greater stability at acidic pH than under basic conditions. A 10 mg/ml solution in water has a pH of approximately 7 and, whilst stable at −20° C. for a period of at least 12 weeks, up to 25% degradation occurs at 4° C. over the same period of time. Dilution into dextrose to a final prodrug concentration of 1 mg/ml affords a solution with a pH of approximately 6 which undergoes less than 5% degradation over a 4 h period at ambient temperature.

Stability to Human Plasma

The stability of the meglumine salts of 3'/4'-((N-carboxymethyl) carbamoyloxy)-3,4'(3'),5,7-tetrahydroxyflavone has been assessed in human plasma by HPLC. Freshly prepared plasma (2.5 ml) was incubated at 37° C. and 0.02 ml of a 6.3 mg/ml solution of the prodrug compound in water was added. Aliquots of plasma were taken for HPLC analysis at zero time and at intervals thereafter. Samples were quenched with chilled methanol, the resulting precipitate was centrifuged at 4° C. at 800 rpm for 5 minutes, and the supernatant was analysed by HPLC.

Both isomers, i.e. both the 3' and 4' carbamate esters, were found to be converted into Quercetin. The half life of each isomer in human plasma was approximately 1 hour.

EXAMPLE

Synthesis of 3'/4'-((N-Carboxymethyl)carbamoyloxy)-3,4'(3'),5,7-tetrahydroxy-flavone, N-Methyl-D-glucamine salt By way of example of the preparation of compounds in accordance with the present invention a process will now be described for the preparation of 3'/4'-[(N-Carboxymethyl)carbamoyloxy]-3,4'(3'),5,7-tetrahydroxyflavone, N-Methyl-D-glucamine salts utilising a 7-step synthesis starting from readily available Quercetin. To achieve a regioselective synthesis the acetylation/benzylation strategy originally reported by Jurd, *J.Am Chem. Soc.,* 80, 5531 (1958), was adapted to allow selective derivatisation of the 3'-position. The different steps or stages in the process are illustrated in the diagram below. Although the primary target product would appear to be the 3' isomer, it was found that after Stage 6 some migration occurs leading to formation also of the 4' isomer so that the final product is a mixture of both 3' and 4' isomers.

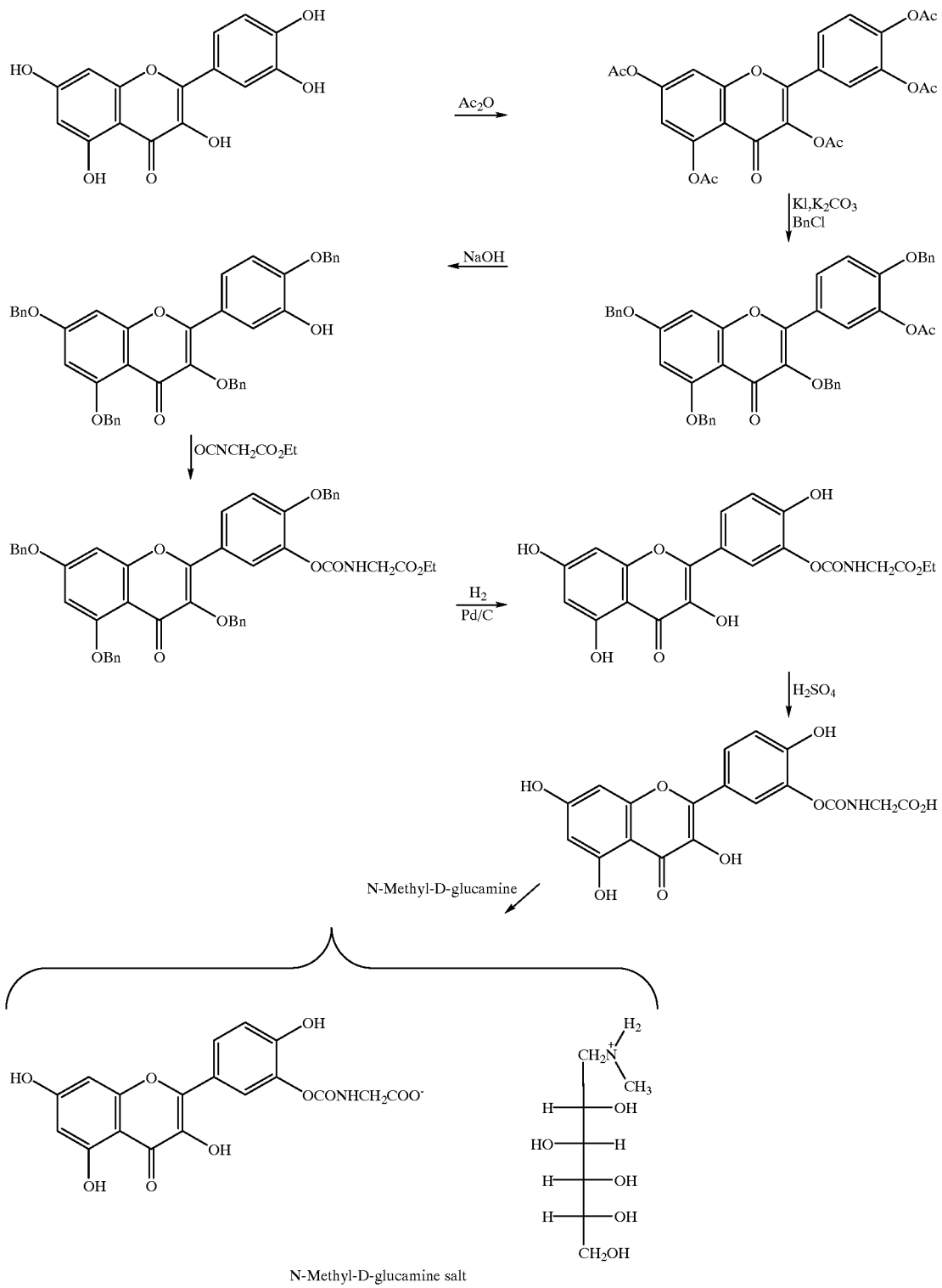

Stage 1—Preparation of 3,3',4',5,7-Pentaacetoxyflavone

Concentrated sulfuric acid (ca 0.05 ml) was added to an ice cold suspension of Quercetin dihydrate (50.02 g, 0.15 mol) in acetic anhydride (300 ml) and an immediate colour change from yellow to orange was observed. The mixture was heated to 90° C. for 0.25 h, then cooled in an ice bath. A heavy, off-white precipitate formed which was collected by filtration, washed with water and dried in vacuo over phosphorus pentoxide at room temperature until no water could be detected by Karl-Fischer titration. Yield 58.1 g (0.11 mol, 77%).

1H-NMR (d$_6$-DMSO) δ DMSO=2.49 ppm: 2.32 (15H, s, 5×CH$_3$), 7.18 (1H, d,J=2.2 Hz, Ar—H), 7.53 (1H, d, J=9.2

Hz, 5'-H), 7.65 (1H, d, J=2.2 Hz, Ar—H), 7.80–7.95 (2H, overlapping multiplets, 2',6'-H).

Stage 2—Preparation of 3'-Acetoxy-3,4',5,7-tetrabenzyloxyflavone 3,3',4',5,7-Pentaacetoxyflavone (54.1 g, 0.11 mol), potassium iodide (4.4 g, 0.026 mol), potassium carbonate (127.5 g, 0.92 mol) and benzyl chloride (120 ml) were heated at reflux in butanone (780 ml) which had been dried over boric anhydride. After 48 h the reaction mixture was allowed to cool to ambient temperature and filtered. The residue was washed with acetone (3×200 ml) and the combined washings and filtrate were evaporated in vacuo. The evaporation residue was recrystallised twice from ethyl acetate/petrol to furnish the required product as an off white solid (62.8 g, 0.089 mol, 84%).

1H-NMR (d$_6$-DMSO) δ DMSO=2.49 ppm: 2.27 (3H, s, CH$_3$), 5.05 (2H, s, Ar—CH$_2$), 5.21 (2H, s, Ar—CH$_2$), 5.24 (4H, s, 2×Ar—CH$_2$), 6.69 (1H, d, J=2.0 Hz, Ar—H), 6.97 (1H, d, J=2.1 Hz, Ar—H), 7.30–7.60 (20H, overlapping multiplets, Ar—H), 7.62 (1H, dd, J=7.1 Hz, Ar—H), 7.79 (1H, d, J=2.2 Hz, Ar—H), 7.91 (1H, dd, J=2.2 Hz, 8.8 Hz, Ar—H).

Stage 3—Preparation of 3'-Hydroxy-3,4',5,7-tetrabenzyloxyflavone

Aqueous sodium hydroxide solution (191 ml of a 10% w/v solution) was added to a solution of 3'-acetoxy-3,4',5,7-tetrabenzyloxyflavone (61.9 g, 0.088 mol) at reflux in methanol/acetone (780 ml of a 2:5 v/v solution). After 1 h the reaction mixture was cooled to ambient temperature, diluted with water (480 ml) and acidified to pH 1 with hydrochloric acid (230 ml of a 2M solution). A yellow precipitate formed which was isolated by filtration, washed with water (3×120 ml), dried in vacuo and recrystallised from ethyl acetate/petrol. Yield 47.4 g (0.072 mol, 81%).

1H-NMR (d$_6$-DMSO) δ DMSO=2.49 ppm: 4.98 (2H, s, Ar—CH$_2$), 5.21 (2H, s, Ar—CH$_2$), 5.23 (2H, s, Ar—CH$_2$), 5.26 (2H, s, Ar—CH2), 6.70 (1H, d, J=2.0 Hz, Ar—H), 6.89 (1H, d, J=2.0 Hz, Ar—H), 7.28–7.58 (20H, overlapping multiplets, Ar—H), 7.62 (2H, dd, J=7.1 Hz, Ar—H), 9.4 (1H, bs, —OH).

Stage 4—Preparation of 3'-((N-Ethoxycarbonylmethyl)carbamoyloxy) -3,4',5,7-tetrabenzyloxyflavone Triethylamine (11 ml) and ethyl isocyanatoacetate (11.8 ml, 13.6 g, 0.11 mol) were added to a suspension of 3'-hydroxy-3,4',5,7-tetrabenzyl-oxyflavone (46.7 g, 0.071 mol) in tetrahydrofuran (425 ml) and the mixture was stirred at 50° C. After 0.5 h the suspended solids dissolved. After a further 18 h a further portion of ethyl isocyanatoacetate (3 ml, 3.5 g, 0.027 mol) was added and stirring continued. After a further 2.5 h the reaction mixture was evaporated in vacuo and the residue was recrystallised from dichloromethane/petrol to furnish N,N'-di(ethoxycarbonylmethyl)urea. The supernatant liquor was evaporated and the residue was recrystallised from ethyl acetate/petrol to furnish the title compound as a white solid (36.5 g, 0.046 mol, 65%).

1H-NMR (d$_6$-DMSO) δ DMSO=2.49 ppm: 1.19 (3H, t, J=7.1 Hz. CH$_3$), 3.88 (2H, d, J=6.0 Hz, NHC$\underline{H}_2$), 4.12 (2H, q, J=7.1 Hz, —OCH$_2$—), 5.03 (2H, s, Ar—CH$_2$), 5.23 (2H, s, Ar—CH$_2$), 5.25 (2H, s, Ar—CH$_2$), 5.26 (2H, s, Ar—CH$_2$), 6.70 (1H, d, J=2.0 Hz, Ar—H), 7.02 (1H, d, J=2.0 Hz, Ar—H), 7.28–7.58 (19H, overlapping multiplets, Ar—H), 7.63 (2H, d, J=6.9 Hz, Ar—H), 7.81 (1H, d, J=2.2 Hz, Ar—H), 7.90 (1H, dd, J=2.2 Hz, 8.8 Hz, Ar—H), 8.29 (1H, t, J=6.1 Hz, —NH—).

Stage 5—Preparation of 3'-((N-Ethoxycarbonylmethyl)carbamoyloxy)-3,4',5,7-tetrahydroxyflavone A solution of 3'-((N-ethoxycarbonylmethyl)carbamoyloxy)-3,4', 5,7-tetrabenzyloxyflavone (24.6 g, 0.031 mol) in THF (460 ml) was shaken under a hydrogen atmosphere (pH$_2$=110 psi) in the presence of palladium on charcoal catalyst (10% w/w Pd, 2.5 g). After 20 h the reaction mixture was filtered and the filtrate evaporated in vacuo to furnish the title compound as a yellow solid (14.7 g) which was contaminated with toluene and THF as judged by 1H-NMR but was considered suitable for use without further drying.

1H-NMR (d$_6$-DMSO) δ DMSO=2.49 ppm: 1.22 (3H, t, J=7.1 Hz, CH$_3$), 3.85 (2H, d, J=6.0 Hz, NHC$\underline{H}_2$), 4.13 (2H, q, J=7.1 Hz, —OCH$_2$—), 6.20 (1H, d, J=2.0 Hz, Ar—H), 6.46 (1H, d, J=2.0 Hz, Ar—H), 7.06 (1H, d, J=8.6 Hz, 5'-H), 7.86–7.93 (2H, overlapping multiplets, 2',6'-H), 8.12 (1H, t, J=6.1 Hz, —NH—), 9.54 (1H, s, —OH), 10.38 (1H, s, —OH), 10.79 (1H, s, —OH), 12.43 (1H, s, —OH).

Stage 6—Preparation of 3'-((N-Carboxymethyl)carbamoyloxy)-3,4',5,7-tetrahydroxyflavone 3'-((N-Ethoxycarbonylmethyl)carbamoyloxy)-3,4',5,7-tetrahydroxyflavone (6.03 g, 0.014 mol) was dissolved in THF (400 ml) and heated to reflux. Sulfuric acid (350 ml of a 2M solution) was added and the reaction mixture was heated at 70° C. The progress of the reaction was monitored by HPLC (Primesphere HC C-18, 5 mm 250×3.2 mm; mobile phase: 34% acetonitrile and 0.04% trifluoroacetic acid in water; flow rate: 0.9 ml/min; detection:UV at 220 nm) at intervals of 0.5 h: the starting ester, the required product and Quercetin were all detected in the reaction mixture. After 2 h the proportion of the desired product appeared to be at a maximum. The reaction mixture was poured into water (1.5 L) and extracted with ethyl acetate (500 ml, 3×200 ml). The ethyl acetate extracts were combined and washed with water (5×100 ml), dried over magnesium sulfate and evaporated in vacuo to furnish the required product as a yellow solid (5.57 g) contaminated with 8% w/w Quercetin and 1%w/w 3'-((N-ethoxycarbonylmethyl)carbamoyloxy)-3,4',5,7-tetrahydroxyflavone as judged by HPLC.

1H-NMR (d$_6$-DMSO) δ DMSO=2.49 ppm: 3.76 (2H, d, J=6.0 Hz, NHC$\underline{H}_2$), 6.19 (1H, d, J=1.9 Hz, Ar—H), 6.46 (1H, d, J=1.9 Hz, Ar—H), 7.05 (1H, d, J=8.5 Hz, 5'-H), 7.88–7.92 (2H, overlapping multiplets, 2',6'-H), 8.04 (1H, t, J=6.1 Hz, —NH—), 9.58(1H, s, —OH), 10.40 (1H, s, —OH), 10.82 (1H, s, —OH), 12.44 (1H, s, —OH), 12.5 (1H, bs, COOH).

Stage 7—Preparation of 3'-((N-Carboxymethyl)carbamoyloxy)-3,4',5,7-tetrahydroxyflavone, N-Methyl-D-glucamine salt A solution of N-methyl-D-glucamine (2.76 g, 0.014 mol) in methanol (200 ml) was added to a solution of 3'-((N-carboxymethyl)carbamoyloxy)-3,4',5,7-tetrahydroxyflavone (5.78 g, 90% pure, 0.013 mol) in methanol (300 ml). The solvent was removed in vacuo and the residue was dissolved in water (500 ml). The solution was adjusted to pH 6.9 with 1M hydrochloric acid, extracted with ethyl acetate (3×50 ml) and freeze dried. The freeze dried solid was redissolved in water (500 ml) and filtered successively through 1.2 μm, 0.45 μm, and 0.2 μm filters and freeze dried once more to furnish the required product as a fine yellow solid (6.12 g, 0.01 mol, 79%).

1H-NMR (D$_2$O) δ HOD=4.8 ppm: 2.69 (3H, s, NCH$_3$), 3.13 (2H, bm, CH$_2$NHCH$_3$), 3.5–3.8 (7H, overlapping multiplets, C$\underline{H}$OH), 4.01 (1H, m, C$\underline{H}$OH), 5.80 (2H, bd, Ar—H, both isomers), 6.67 (1H, d, Ar—H, major isomer), 6.90 (1H, d, Ar—H, minor isomer), 7.20 (2H, overlapping multiplets, Ar—H, minor isomer), 7.41 (2H, overlapping multiplets, Ar—H, major isomer).

IR (KBr disc) υ=3360 (OH, NH), 2931, 1715 (C=O), 1655 (C=O), 1598 (C=O), 1561, 1514, 1461, 1424, 1383, 1315, 1248, 1189, 1166, 1087, 1043 cm$^{-1}$.

FAB$_{m/z}$=635, 599 ((M+H)$^+$), 598 (M$^+$), 586, 460, 440, 427, 404, 391, 307, 303, 287, 196 (N-methylglucamine+H)$^+$.

Although the final product is a mixture of the 3' and 4' isomers, these can be separated if desired, e.g. by HPLC, but since both can act as prodrugs that degrade to Quercetin, separation will generally be unnecessary. The final product may also contain a certain amount of the N-methyl-D-glucamine, but again this is considered unlikely to interfere with the desired Quercetin prodrug characteristics of the product.

N-alkylated carbamates for use in other embodiments where R$^6$ is alkyl may be prepared by reaction of phenols with reagents of the type RR'NCOCl which are conveniently prepared in situ by reaction of the appropriate amine with phosgene. Alternatively they may be prepared by reaction of amines of the type RR'NH with aryl chloroformates ArOCOCl, which are themselves prepared in situ by reaction of phenols with phosgene. Thus ArOC(O)NRCH$_2$CO$_2$Et for example may be prepared by reaction of ArOH with RNHCH$_2$CO$_2$Et in the presence of phosgene or triphosgene.

In preparing amine salts of Quercetin analogues or derivatives in accordance with the invention using an amino sugar, various amino sugars other than the N-methyl-D-glucamine hereinbefore mentioned may of course be used instead. A non-exhaustive list of amino sugars suitable for forming such salts is given below A 1-Amino-1-deoxy-D-sorbitol
B N-Methyl-D-glucamine (meglumine)
C 1-Deoxy-1-(methylamino)-D-galactitol
D 1-Deoxy-1-(octylamino)-D-glucitol
E 1-Deoxy-1-(2-hydroxyethylamino)-D-glucitol
F Disorbitylamine
G D-Galactosamine
H D-Glucosamine
I D-Mannosamine The structures of the above compounds A–I are illustrated in the diagrams at the end of the present description which are labelled to correspond.

Therapeutic Use

As already indicated, the novel analogues or derivatives of Quercetin provided by the present invention, especially such analogues or derivatives which are biodegradable in vivo to Quercetin and which are soluble in water, are particularly useful as prodrugs that may be made up into pharmaceutical formulations for administration in therapeutic treatment, for example therapeutic treatment of mammals suffering from neoplastic diseases or cancer.

In making up such pharmaceutical formulations in the form of sterile liquid preparations for parental use for instance, a predetermined therapeutically effective non-toxic amount of the particular analogue or derivative concerned may be dissolved in phosphate buffered saline and the preparations may be presented in unit dosage form and contained in sealed ampoules ready for use as an intravenous infusion. In general, at least in aqueous solution, concentrations equivalent to those that have been used for Quercetin will be preferred, but the amount and dosage routine required for optimum effectiveness will of course vary and is ultimately at the discretion of the medical or veterinary practitioner treating the mammal in each particular case.

As will be seen, the invention provides a number of different aspects and, in general, it embraces all novel and inventive features and aspects, including novel compounds, herein disclosed either explicitly or implicitly and either singly or in combination with one another. Moreover, the scope of the invention is not to be construed as being limited by the illustrative examples or by the terms and expressions used herein merely in a descriptive or explanatory sense.

A
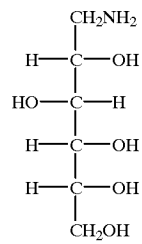

B
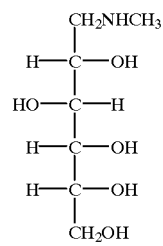

C
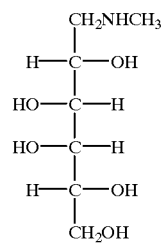

D
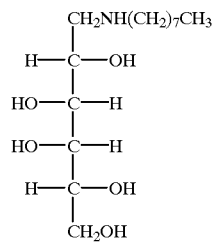

E
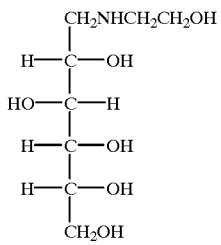

F
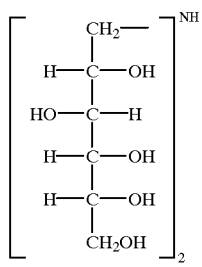

-continued

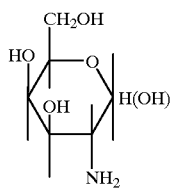

G

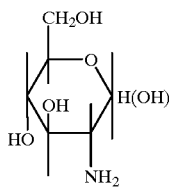

H

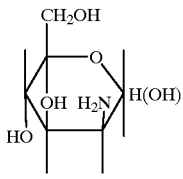

I

What is claimed is:

1. A compound having the structural formula I

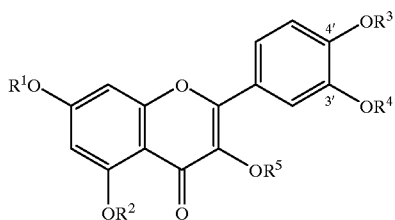

I or a pharmaceutically acceptable salt thereof,
wherein
one of $R^1$, $R^2$, $R^3$, $R^4$ and $R^5$ is an amino acid carbamate group $CONHCH(R^6)CO_2H$ and the remainder are each hydrogen, and wherein $R^6$ is hydrogen or $C_{1-4}$ lower alkyl.

2. The compound of claim 1 wherein $R^6$ is methyl.

3. The compound of claims 2 or 3 wherein each of $R^1$, $R^2$, $R^3$ and $R^5$ is hydrogen, and $R^4$ is $CONHCH_2COOH$.

4. The compound of claims 1 or 2 wherein each of $R^1$, $R^2$, $R^4$ and $R^5$ is hydrogen, and $R^3$ is $CONHCH_2COOH$.

5. The compound of claims 1 or 2 in the form of an alkali metal salt, an ammonium salt or an amine salt.

6. The compound of claim 5 in the form of an amine salt which is formed with an amino sugar.

7. The compound of claim 5 in the form of an amine salt which is formed with an N-alkyl amino sugar.

8. The compound of claim 7 in wherein said amino sugar is N-methyl-D-glucamine.

9. The compound of claim 6 wherein said amino sugar is selected from 1-amino-1-deoxy-D-sorbitol, N-methyl-D-glucamine(meglumine), 1-deoxy-1-(methylamino)-D-galactitol, 1-deoxy-1-(octylamino)-D-glucitol, 1-deoxy-1-(2-hydroxyethylamino)-D-glucitol, disorbitylamine, D-galactosamine, D-glucosamine and D-mannonsamine.

10. A prodrug composition comprising a mixture of the compound of claim 5 wherein $R^4$ is $CONHCH_2COOH$ and the compound of claim 5 wherein $R^3$ is $CONHCH_2COOH$.

11. A method of treating a mammal suffering from a neoplastic disease or cancer comprising administering to said mammal a compound according to claim 1 or a composition according to claim 10.

12. A pharmaceutical composition comprising a therapeutically effective non-toxic amount of the compound of claim 1 or the prodrug composition of claim 10 and a compatible pharmaceutically acceptable carrier, diluent or excipient.

13. The pharmaceutical composition of claim 12 containing a Quercetin carbamate ester that is biodegradable in vivo to Quercetin.

14. The pharmaceutical composition of claim 12 in the form of a sterile liquid preparation presented in unit dosage form.

15. The pharmaceutical composition of claim 14 in which said compound or prodrug composition is dissolved in phosphate-buffered saline.

16. A method of treating a mammal suffering from a neoplastic disease or cancer comprising administering to said mammal the pharmaceutical composition of claim 12.

17. The pharmaceutical composition of claim 13 in the form of a sterile liquid preparation presented in unit dosage form.

18. The pharmaceutical composition of claim 17 in which said compound or prodrug composition is dissolved in phosphate-buffered saline.

19. A method of treating a mammal suffering from a neoplastic disease or cancer comprising administering to said mammal the pharmaceutical composition of claim 13.

20. A method of treating a mammal suffering from a neoplastic disease of cancer comprising administering to said mammal the pharmaceutical composition of claim 14.

21. A method of treating a mammal suffering from a neoplastic disease of cancer comprising administering to said mammal the pharmaceutical composition of claim 15.

22. A prodrug composition comprising a mixture of 3'-((N-carboxymethyl)carbamoyloxy)-3,4',5,7-tetrahydroxyflavone, N-Methyl-glucamine salt and 3'-((N-carbolymethyl)carbamoyloxy)-3,3',5,7-tetrahydroxyflavone, N-Methylglucamine salt, biodegradable to Quercetin.

* * * * *

UNITED STATES PATENT AND TRADEMARK OFFICE
CERTIFICATE OF CORRECTION

PATENT NO. : 6,258,840 B1 Page 1 of 1
DATED : July 10, 2001
INVENTOR(S) : Golding et al.

It is certified that error appears in the above-identified patent and that said Letters Patent is hereby corrected as shown below:

Column 2,
Line 63, (Table HPLC) please insert -- Under the same chromatographic conditions, Quercetin has a retention time of 22.8 minutes --;

Column 11,
Line 47, please delete "2 or 3" and insert -- 1 or 2 -- therefore;

Column 12,
Line 52, please delete "carbolymethyl" and insert -- carboxymethyl -- therefor;

Signed and Sealed this

Nineteenth Day of November, 2002

*Attest:*

*Attesting Officer*

JAMES E. ROGAN
*Director of the United States Patent and Trademark Office*